(12) United States Patent
Gicquel et al.

(10) Patent No.: US 6,958,130 B1
(45) Date of Patent: Oct. 25, 2005

(54) AUTOMATED APPARATUS FOR IMMUNOLOGICAL ASSAY

(75) Inventors: Thierry Gicquel, Courdimanche; Edouard Lentwojt, Saint-Leu D'Esserent, both of (FR)

(73) Assignee: Laboratories Merck-Clevenot, Cedex (FR)

(*) Notice: Subject to any disclaimer, the term of this patent is extended or adjusted under 35 U.S.C. 154(b) by 0 days.

(21) Appl. No.: 08/953,854

(22) Filed: Oct. 15, 1997

(30) Foreign Application Priority Data

Oct. 15, 1996 (FR) .......................................... 96 12546

(51) Int. Cl.[7] .............................................. G01N 35/04
(52) U.S. Cl. ........................ 422/65; 422/63; 422/64; 436/43; 436/47; 436/48
(58) Field of Search ...................... 422/63, 64, 65, 422/67; 436/43, 47, 48

(56) References Cited

U.S. PATENT DOCUMENTS

| | | | | |
|---|---|---|---|---|
| 4,236,825 A | * | 12/1980 | Gilford et al. ............... | 356/414 |
| 4,265,855 A | * | 5/1981 | Mandle et al. ................ | 422/65 |
| 4,578,244 A | * | 3/1986 | Cosgrove, Jr. et al. ....... | 422/65 |
| 4,710,352 A | * | 12/1987 | Slater et al. .................. | 422/63 |
| 4,731,225 A | * | 3/1988 | Wakatake ..................... | 422/65 |
| 4,882,127 A | * | 11/1989 | Rosenthal et al. ............ | 422/50 |
| 5,096,670 A | * | 3/1992 | Harris et al. .................. | 422/65 |
| 5,232,665 A | * | 8/1993 | Burkovich et al. ........... | 422/65 |
| 5,397,539 A | * | 3/1995 | Hayashi et al. ............... | 422/65 |

FOREIGN PATENT DOCUMENTS

| | | |
|---|---|---|
| EP | 0 061 431 | 9/1982 |
| FR | 2 247 719 | 5/1975 |
| JP | 06265559 | 9/1994 |
| WO | WO 91/07662 | 5/1991 |
| WO | WO 96/14582 | 5/1996 |

* cited by examiner

Primary Examiner—Long V. Le
(74) Attorney, Agent, or Firm—Morgan, Lewis & Bockius LLP

(57) ABSTRACT

An automated immunological assay apparatus is disclosed. The apparatus includes a frame carrying device for supporting samples to be analyzed, a device for supporting reagents, and a device for displacing sets of reaction wells along a rectangular path. A cog belt extends along the long sides of the path and a mechanism for transverse displacement extends along the short sides of the path. A device is also provided at one end of the path for automatically feeding sets of reaction wells.

11 Claims, 7 Drawing Sheets

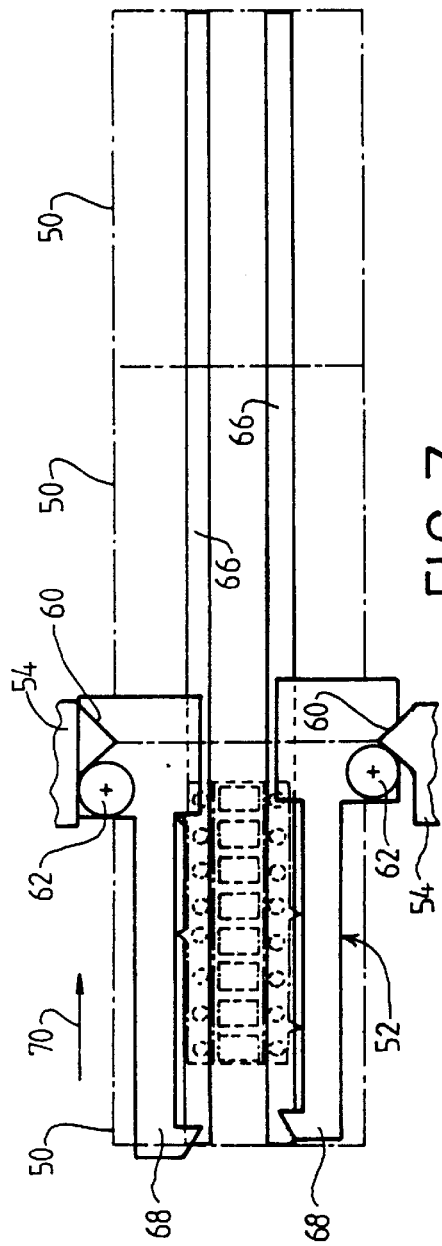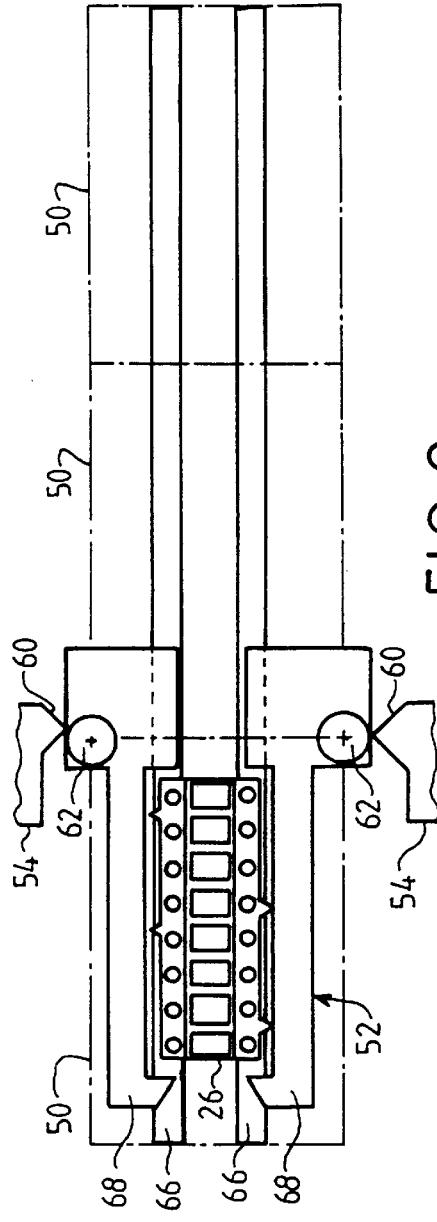

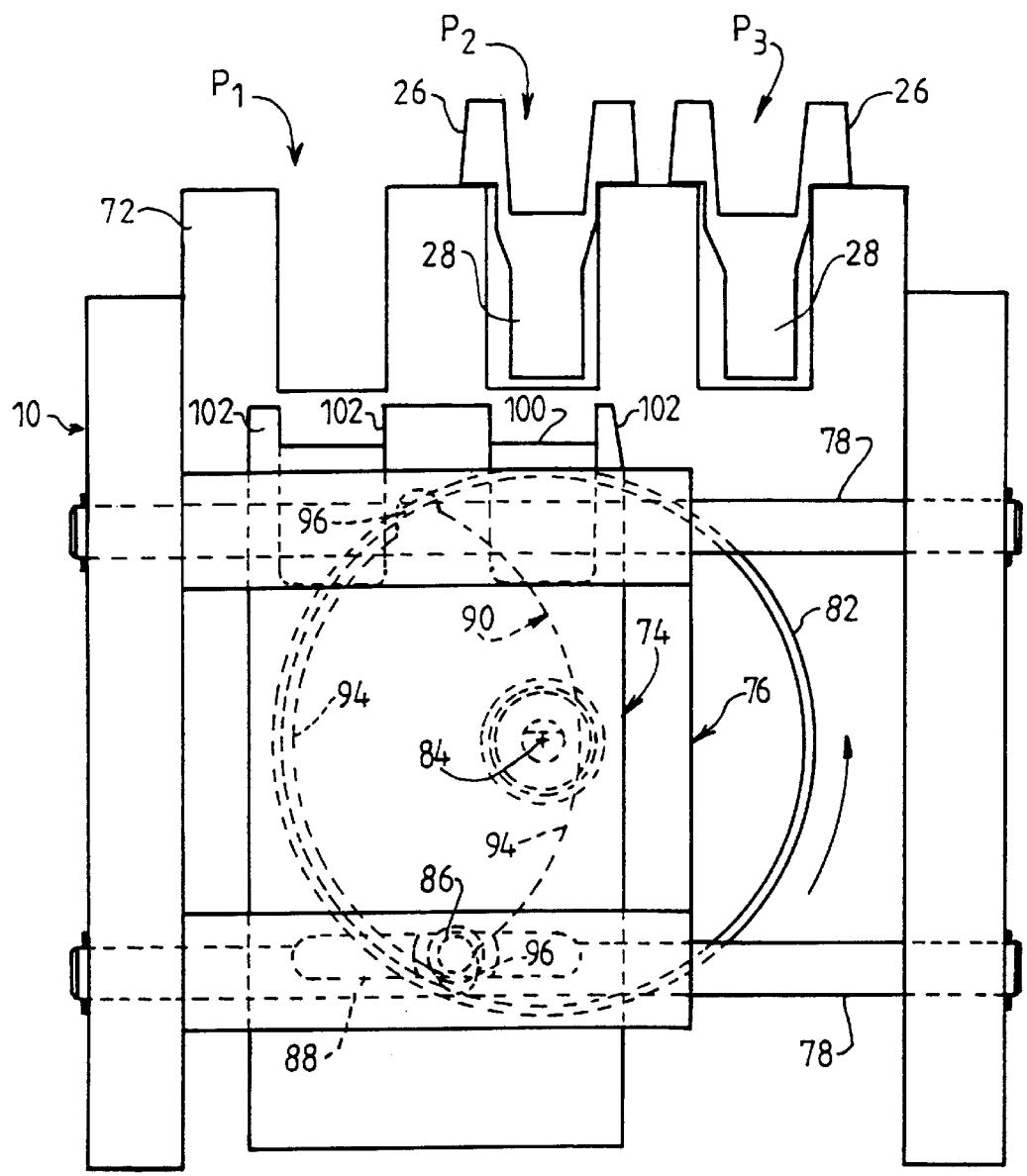
FIG.9
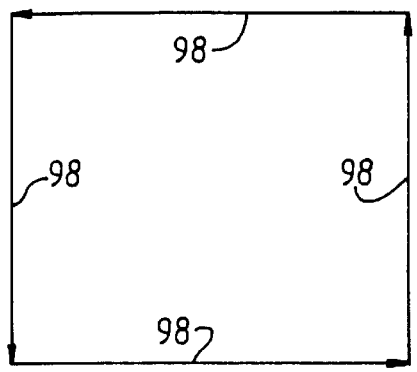

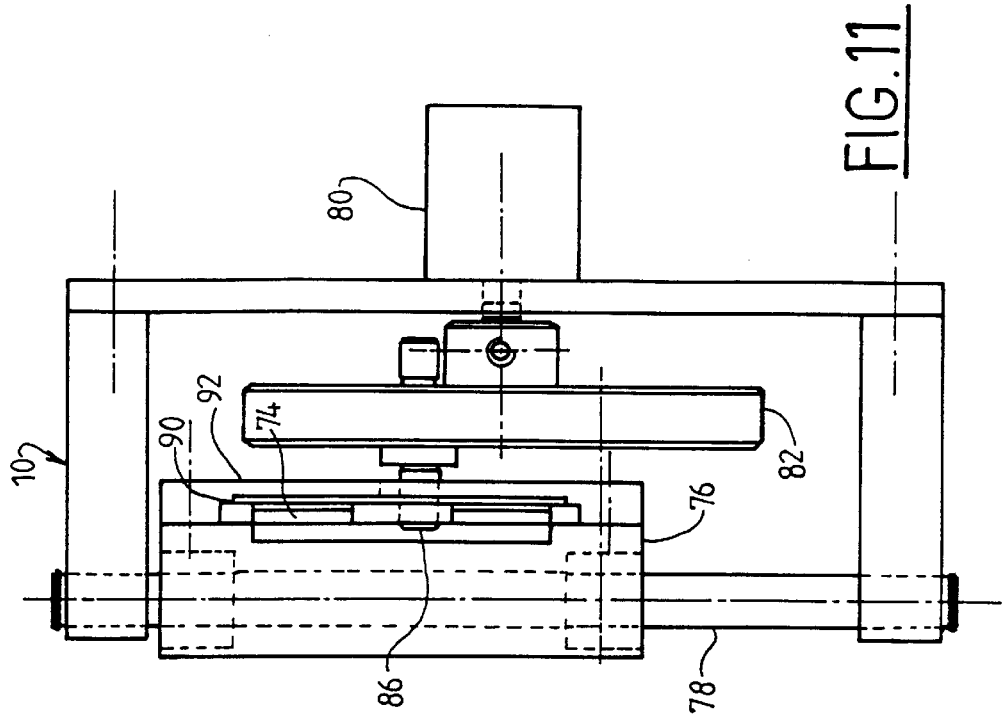
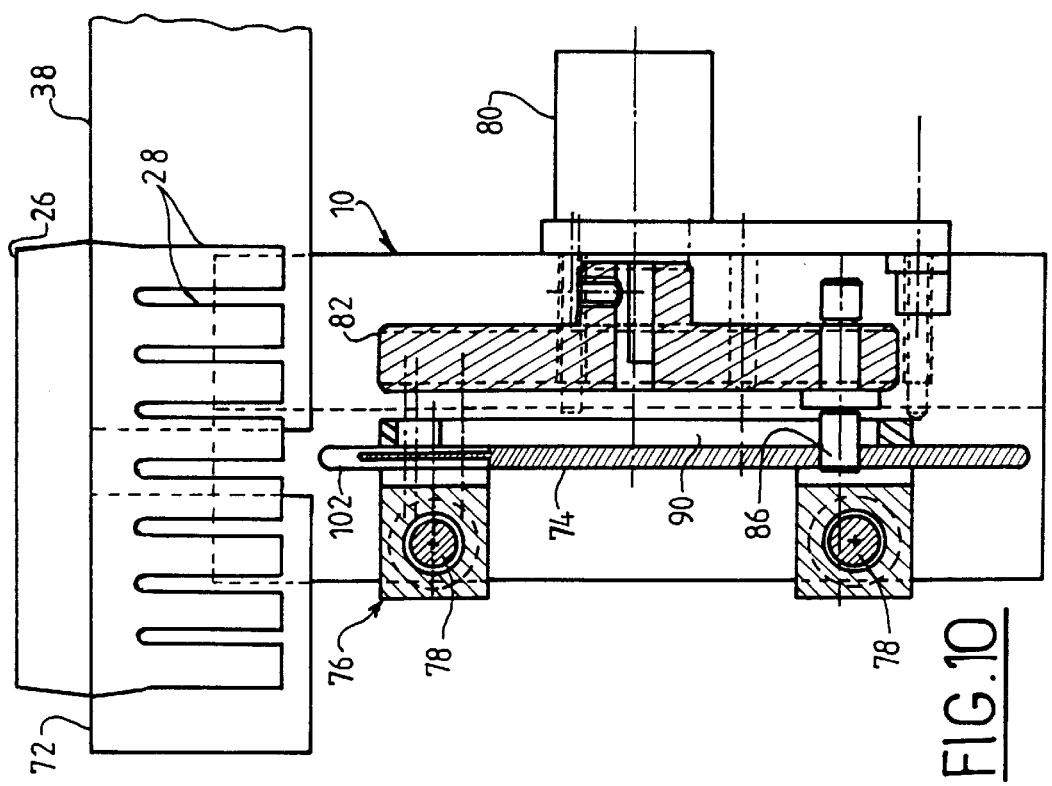

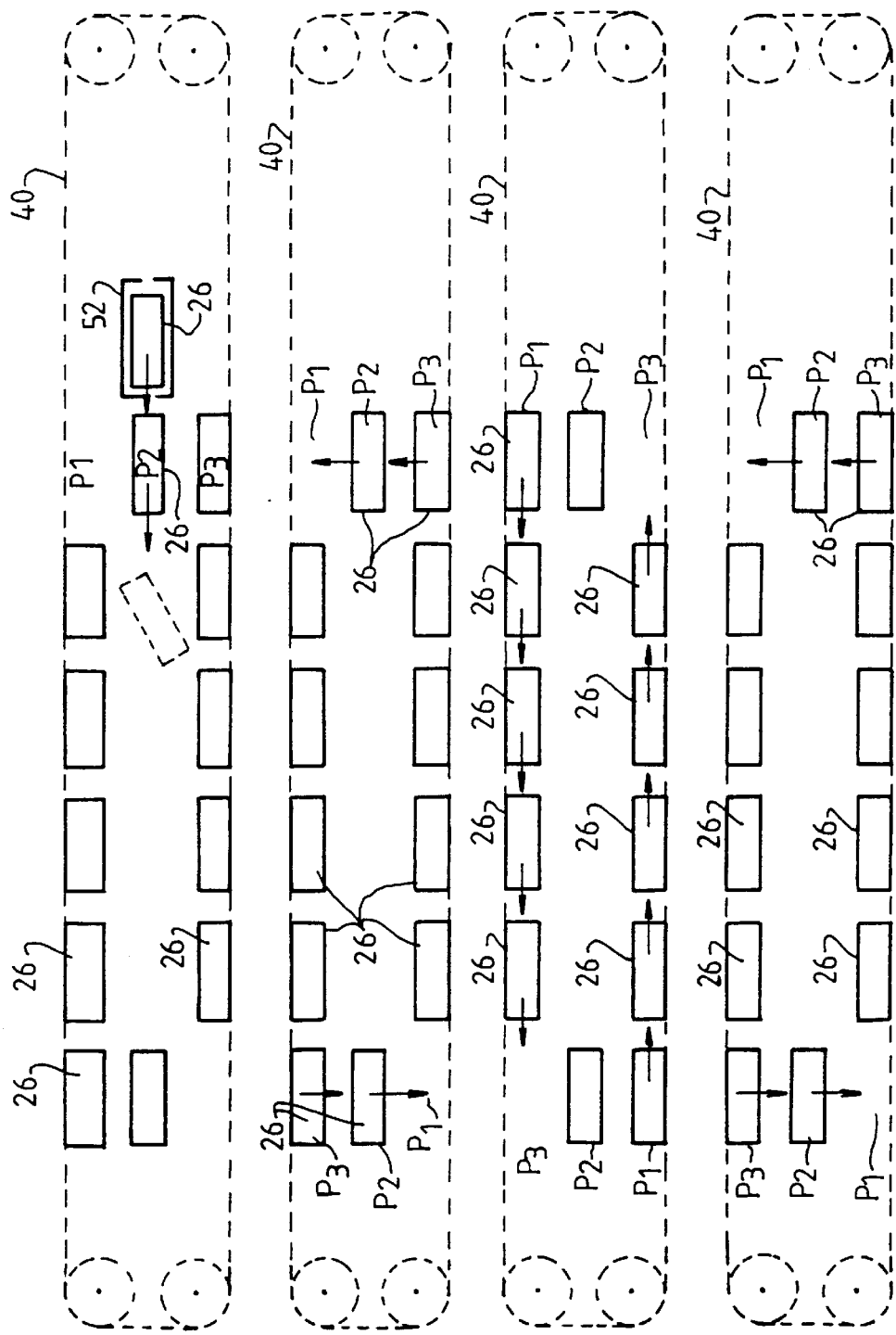

AUTOMATED APPARATUS FOR IMMUNOLOGICAL ASSAY

The invention relates to apparatus for immunological assay of various substances in biological samples, and enabling assay methods of the ELISA, RIA, FIA, LIA, FPIA, CLIA, etc. types to be automated.

BACKGROUND OF THE INVENTION

Apparatuses of this type have already been described in international applications WO 91/07662 and WO 96/14582 to which reference may be made for a description of the assays performed, those known apparatuses essentially comprising means for supporting, guiding, and displacing reaction wells stepwise along a path comprising a predetermined number of positions, a turntable for supporting samples to be analyzed, a turntable for supporting reagents, means for taking determined quantities of samples and of reagents and for injecting these quantities into the reaction wells, means for washing the wells, means for optically reading assay results, and a controlling computer system enabling previously-programmed analysis cycles to be performed corresponding to assays of the single-reagent type or of the two-reagent type, the first of said known apparatuses operating at a rate of about 120 assays per hour, while the second operates at about 360 assays per hour.

The apparatus described in international application WO 96/14582 is further distinguished in that it is designed to operate with reaction modules constituted by molded plastics parts each comprising an aligned plurality of reaction wells that are integrally secured with one another, said reaction modules being mass-produced at very low cost, thereby enabling them to be disposed of after being used once only. In addition, those reaction modules are stackable, thus making them easier to package and also facilitating stacking of the modules in automated feed means of the apparatus.

That known apparatus is also characterized by means for guiding and displacing reaction modules along an open loop track that is U-shaped, with means for automatically feeding reaction modules being provided at one end, and means for automatically ejecting reaction modules being provided at the other.

That apparatus has the advantage of operating at a high rate (360 assays per hour), but it is bulkier and more expensive than the apparatus described in international application WO 91/07662.

OBJECTS AND SUMMARY OF THE INVENTION

The present invention seeks to provide an automated apparatus for immunological assay which enables the advantages of both of those known apparatuses to be combined while avoiding their drawbacks.

To this end, the invention provides an apparatus of the above-specified type comprising means for supporting, guiding, and displacing sets of reaction wells stepwise along a path comprising a predetermined number of positions, means for supporting samples to be analyzed, means for supporting reagents, means for taking determined quantities of samples and of reagents and for injecting these quantities into the reaction wells, and means for washing the wells, means for reading the results, and means for feeding sets of reaction wells and for ejecting used sets of wells, wherein the path for the sets of reaction wells is rectangular in shape comprising two long sides defined by parallel rectilinear rails for supporting and guiding sets of wells, and two short sides defined by means for displacing sets of wells transversely through three positions comprising two end positions on the long sides of the above-mentioned path and one intermediate position which constitutes the ejection position for a used set of wells and the feed position for a new set of wells.

In the invention, the means for displacing sets of wells are simpler and more reliable than those used in the prior art, particularly because the trajectories of the sets of wells are rectilinear and do not include curved portions, with the transfer of the sets of wells between the three positions provided on the short sides of their path making it possible to simplify both delivery of new sets of wells and automated ejection of used sets of wells.

According to another characteristic of the invention, the means for displacing the sets of wells transversely are actuated during intervals between two displacement steps of the sets of wells along the long sides of the above-mentioned path.

In a preferred embodiment of the invention, the means for displacing the sets of wells along the long sides of the above-mentioned path comprise a cog belt engaging ribs of longitudinal rims on the sets of wells, said belt being guided along the outer rail of each long side of the above-mentioned path, whereas the transverse displacement means comprise grasping means for taking two sets of wells and means for lifting, displacing transversely, and lowering the grasping means, with the grasping means comprising a transverse vertical plate that can be displaced beneath the sets of wells and that can be engaged between two wells in a set to lift the set off support rails and move the set from one position to the other.

The means for feeding new sets of wells comprise magazines for storing stacks of sets of wells interfitting in one another, a carriage for capturing and horizontally displacing a set of wells, guided beneath the open bottom ends of the magazines and displaceable to the above-mentioned intermediate position forming the feed and ejection position, the magazines being fitted with pivoting arms which hold the bottom set of wells in each stored stack and which are spread apart by the carriage as it passes beneath the stack in order to release the bottom set of wells from the stack and allow it to fall under gravity into a housing formed in the carriage, providing the housing is not already occupied by another set of reaction wells.

The means for ejecting used sets of wells comprise a slideway or a chute opening formed in alignment with the above-mentioned intermediate position, such that the feed means delivering a new set of wells into said intermediate position causes the used set of wells occupying said intermediate position to be pushed to the slideway or chute opening.

In general, the apparatus of the invention benefits from all of the advantages associated with using modular reaction well sets as described in international application WO 96/14582, while simplifying the means for displacing the sets of wells and reducing the bulk thereof, and it conserves the advantages of cost associated with the apparatus described in international application WO 91/07662 while simplifying and improving the use of that apparatus.

BRIEF DESCRIPTION OF THE DRAWINGS

The invention will be better understood and other characteristics, details, and advantages thereof will appear more clearly on reading the following description given by way of example and made with reference to the accompanying drawings, in which:

FIGS. 7 and 8 are fragmentary diagrammatic plan views showing how the feed means operate;

FIG. 9 is a diagrammatic vertical cross-section view of means for displacing sets of wells transversely;

FIGS. 10 and 11 are diagrammatic views respectively in vertical longitudinal section and in plan showing the transverse displacement means; and FIGS. 12 to 15 are diagrams showing the operation of the means for displacing sets of wells in the apparatus of the invention.

MORE DETAILED DESCRIPTION

Figure 1:
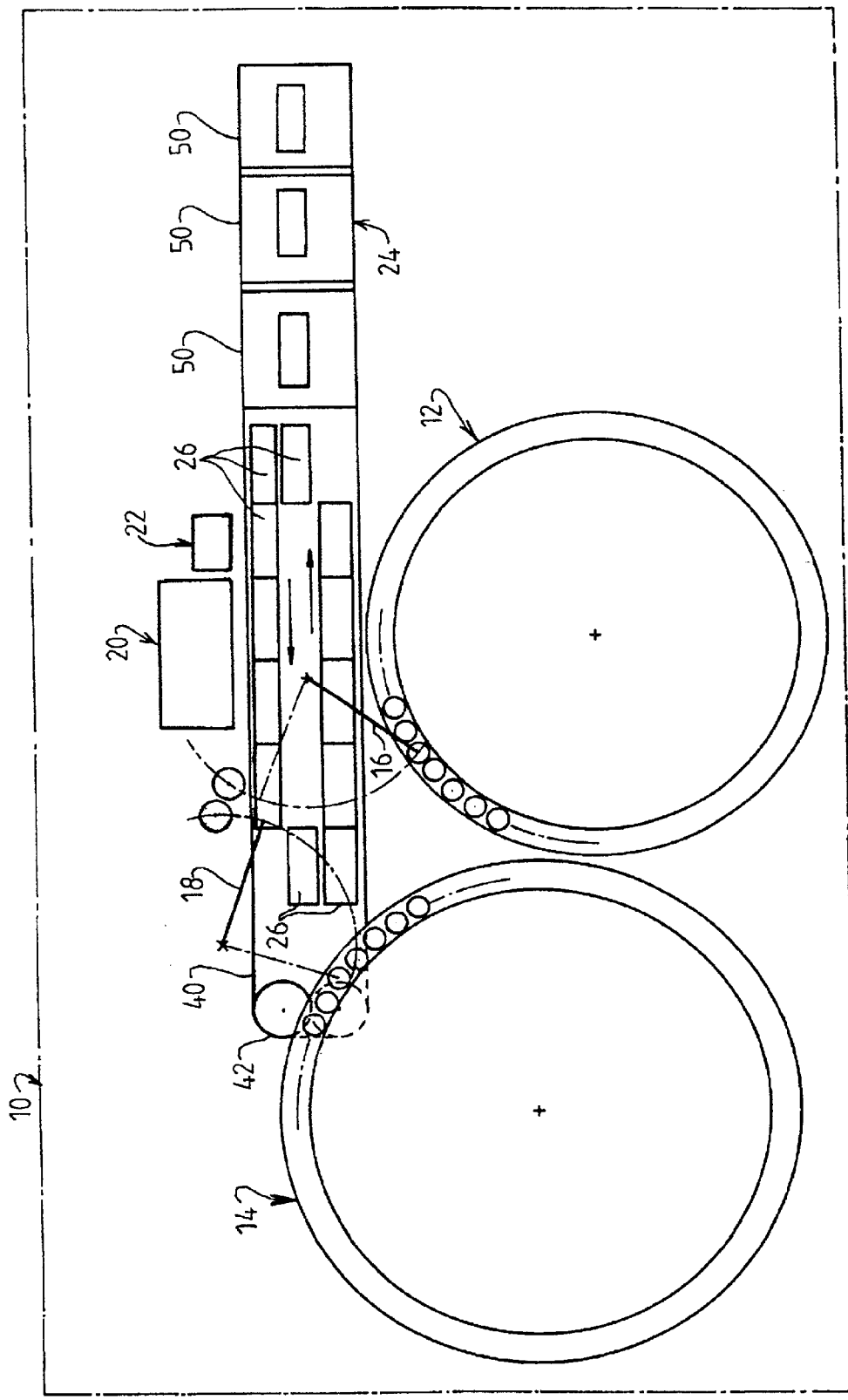
FIG. 1 is a diagrammatic plan view of apparatus of the invention.
Figure 3:
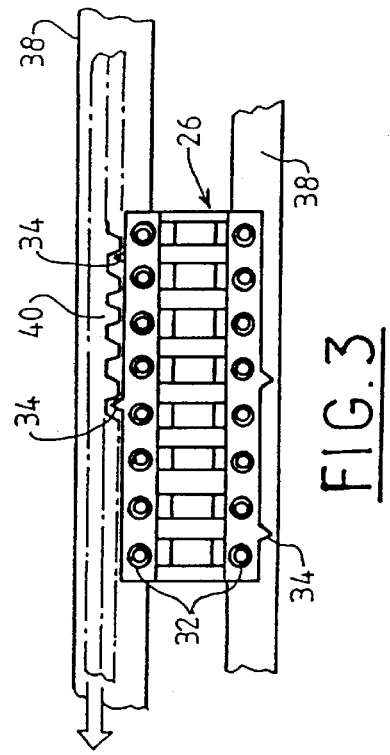
FIG. 3 is a fragmentary diagrammatic plan view of means for supporting and driving a set of wells.
Figure 5:
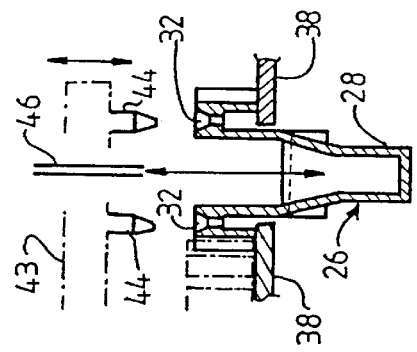
FIGS. 4 and 5 are an elevation view and a cross-section view showing diagrammatically the means for positioning a set of wells.
Figure 2:
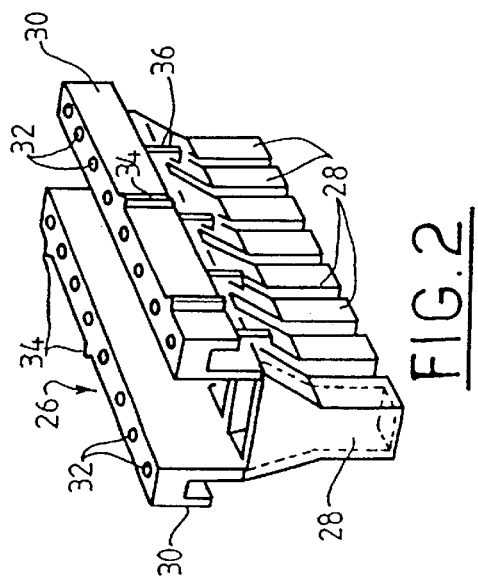
FIG. 2 is a diagrammatic perspective view of a set of reaction wells.
Figure 4:
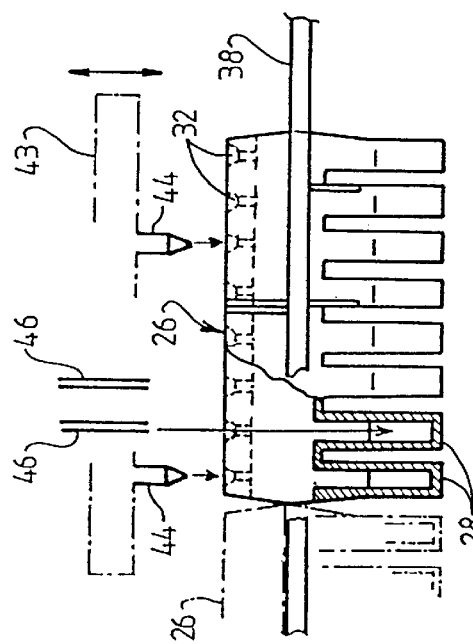

The apparatus of the invention whose general structure is shown very diagrammatically in FIG. 1 comprises a frame 10 on which there are mounted a turntable 12 for supporting samples that are to be analyzed, a turntable 14 for supporting assay reagents, means 16 and 18 for taking a determined quantity of sample and a determined quantity of reagent, respectively, and for depositing these quantities in a reaction well, which means are of the same type as that described in international application WO 96/14582, the content of which is incorporated herein by reference.

The reagents used are of the magnetic bead type, and the apparatus of the invention includes means 20 for washing and rinsing the magnetic beads, which means are of the same type as those already described in the above-mentioned international applications and comprise vertically displaceable needles for sucking and injecting liquid, together with permanent magnets disposed on either side of the path of the reaction wells so as to attract the magnetic beads of the reagents by magnetic attraction and hold them temporarily against the walls of the reaction wells. The means 20 also comprise a needle for depositing a substrate in the reaction wells, and disposed immediately upstream from needles for injecting and sucking washing liquid.

Means 22 for optically reading assay results, of the same type as those already described in the above-mentioned international applications are disposed on the frame 10 in the vicinity of the injection and washing means 20.

The apparatus of the invention also comprises means for displacing sets of reaction wells along a path of rectangular shape, having at one end thereof means 24 for automatically feeding sets of reaction wells and for ejecting said wells, which means are described in greater detail below.

The sets of reaction wells and their displacement and positioning means are shown diagrammatically in FIGS. 2 to 5.

The sets 26 of reaction wells (see FIG. 2) are implemented as single parts by molding a transparent plastics material, with each set comprising eight interconnected reaction wells 28 in alignment on the longitudinal axis of the set 26, each set having two longitudinal top rims 30 that are L-shaped and that extend up from the open ends of the wells 28.

In association with each well 28, each of the longitudinal rims 30 has a tapering orifice 32 for accurately positioning the set 26 in some of the workstations of the apparatus of the invention, and each of the outside side faces of the rims 30 has two vertical ribs 34 designed to co-operate with the means for driving the sets 26.

As already described in international application WO 96/14582, the wells 28 are lengths of rectangular section tube, closed at their bottom ends and flared at their top ends, thereby enabling the sets 26 to be stacked, with partial interfitting between adjacent sets, the bottom portions of the wells 28 in one set 26 penetrating into the flared top ends of the wells 28 of a lower set of reaction wells. Such interfitting is facilitated by the fact that the inside faces of the longitudinal rims 30 diverge slightly away from one another starting from the open top ends of the wells 28.

Vertical ribs 36 are formed on the flanks of the flared top ends of the wells 28 and extend downwards a short distance, with the bottom ends of the ribs 36 being designed to come into abutment against the top faces of the rims 30 of an immediately lower set 26 in a vertical stack of sets of reaction wells.

Along the long sides of their rectangular path through the apparatus, the sets 26 of wells have their longitudinal rims 30 resting on parallel rectilinear rails or bars 38 between which the wells 28 are located. A cog belt 40 is guided over the outer rail 38 of both long sides of the above-specified path, and it passes over four pulleys, two of which are transversely juxtaposed at the location 42 shown in FIG. 1, and the other two of which are transversely juxtaposed at the same end as the feed means 24, with one of the pulleys being a drive pulley for moving the sets 26 of wells stepwise over distances equal to the pitch of the reaction wells 28.

The cogs of the belt 40 engage the vertical ribs 34 of the longitudinal rims 30 on the sets 26 of wells which are displaced by sliding along the rails 38 without requiring significant force, given their small weight and the low level of friction between the materials constituting the sets 26 and the rails 38.

Means are provided for accurately positioning sets 26 on their path through the apparatus at locations where substances need to be placed in the reaction wells or to be removed therefrom.

These positioning means are disposed at the washing means 20. They comprise horizontal plates 43 which are vertically displaceable and which include on their bottom faces rows of vertical fingers 44 designed to be engaged in the orifices 32 in the vertical rims of the sets 26 of wells, in order to position them accurately both longitudinally and transversely relative to injection or suction needles 46 that can thus be lowered into the reaction wells 28 close to the bottoms of the wells without running the risk of coming into abutment against a solid wall.

Figure 6:
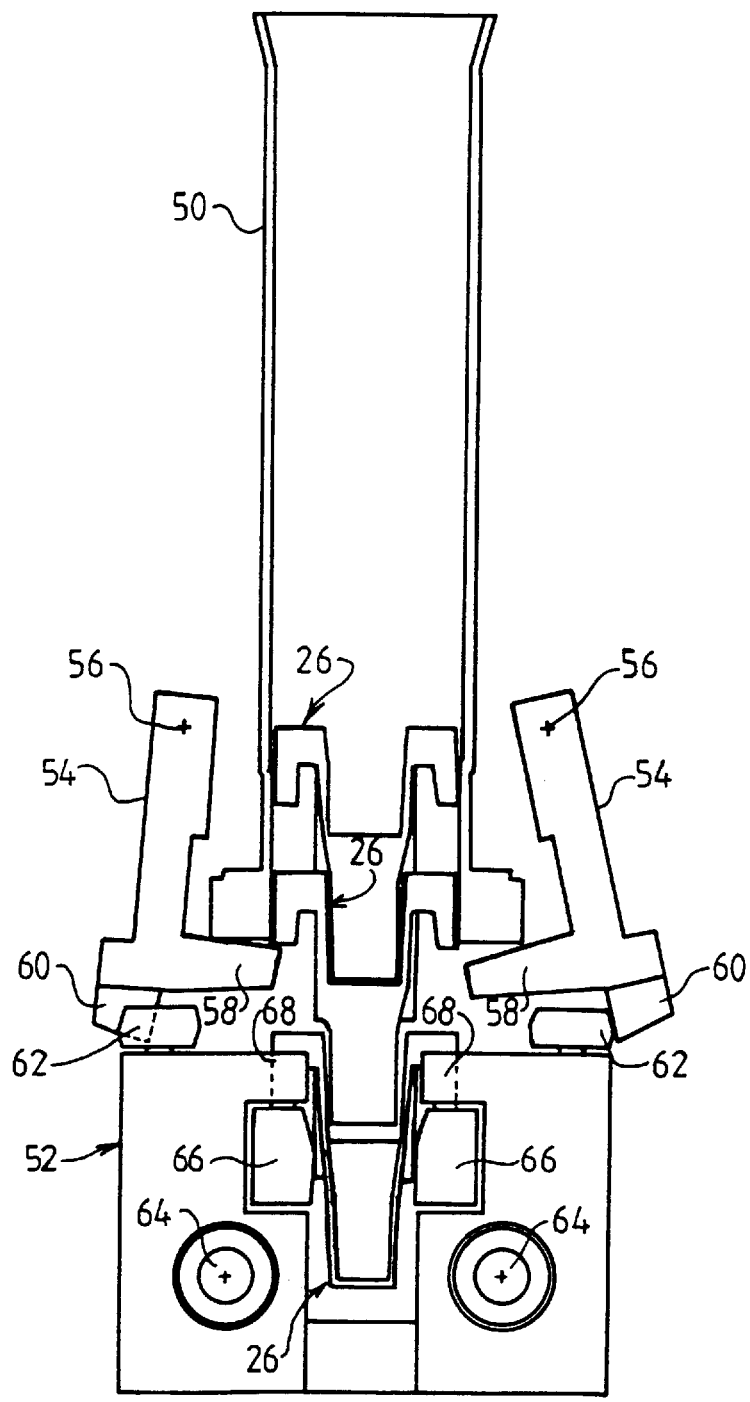
FIG. 6 is a diagrammatic vertical section view of means for feeding sets of reaction wells.

The structure and the operation of the means 24 for feeding new sets of wells are shown diagrammatically in FIGS. 6 to 8.

These means 24 comprise three magazines 50 containing vertical stacks of sets 26 of wells interfitting in one another, the magazines 50 being vertical ducts with open top ends to enable a stack of sets 26 of wells to be loaded therein, and with open bottom ends for placing a single set 26 of wells on a carriage 52 for conveying the set to a feed position provided at one end of the above-mentioned rectangular path.

Each magazine 50 is fitted with two vertical arms 54 pivotally mounted about horizontal axes 56 and carrying perpendicular fingers 58 at their bottom ends for engaging beneath the bottom ends of the magazines 50 to hold the bottom set in a vertical stack of sets 26 contained in the magazine, the bottom set 26 being carried by its vertical rims 30 which rest on the ends of the fingers 28 of the arms 54.

Each of the arms 54 has a heel 60 for co-operating with a wheel 62 of the carriage 52 such that when the wheels 62 go past the heels 60, they move the arms 54 outwards to allow the bottom assembly 62 of a stack contained in the magazine 50 to escape. Return springs (not shown) serve to return the arms 54 to a substantially vertical position against the magazine 50 in order to retain the stack of sets 26 once the heels 60 have been released by the wheels 62.

The carriage 52 is moved in horizontal translation beneath the magazines 50 by two threaded rods 64 rotated by an electric motor and in screw engagement in nuts secured to the carriage 52.

Two rails 66 extend parallel to the threaded rods 64 in recesses formed in the carriage 52 and serve to support the longitudinal rims 30 of the set 26 of reaction wells that have been released from a stack in a magazine 50 and that has fallen under gravity into a housing defined in the carriage 52 by two longitudinal arms 68 (FIGS. 7 and 8), the front and rear ends of the housing being open so that the carriage 52 can move under the magazines 50 without striking the bottom portions of the reaction wells in the stacks of sets 26 contained in the magazines 50 (FIG. 6).

The means 24 for feeding sets 26 of wells operate as follows:

Starting with the carriage 52 in its furthest forward position (position for feeding sets of wells to the rectangular path), it begins by reversing towards the first magazine 50 which contains a stack of sets 26 whose bottom set 26 is shown in dashed lines in FIG. 7. While the carriage 52 is reversing in the direction indicated by arrow 70, its wheels 62 come into abutment against the heels 60 of the arms 54 of the first magazine 50 (top half of FIG. 7) and begin to move them outwards (bottom half of FIG. 7). Once the arms 54 are spread fully apart (FIG. 8), they release the bottom set 26 from the stack contained in the magazine 50, which bottom set moves down under gravity and drops into the housing provided in the carriage 52. The carriage 52 continues to move in reverse in the direction indicated by arrow 70, with its wheels 62 releasing the arms 54 of the first magazine 50, so the arms move back towards each other under drive from their return springs, causing their fingers 58 to engage beneath the longitudinal rims 30 of the bottom set 26 of reaction wells.

The displacement speed of the carriage 52 and the distance through which a set 26 falls are defined so that the passage of the wheels 62 against the heels 60 of the arms 54 releases a single set 26 of wells and prevents two sets 26 of wells dropping into the carriage 52.

Thereafter, the carriage 52 continues to move in reverse in the direction indicated by arrow 70 in order to pass beneath the other magazines 50, spreading the arms 54 thereof by means of its wheels 62 and thus releasing the bottom set 26 of reaction wells from each of the stacks contained in the magazines 50. Nevertheless, the sets 26 released in this way cannot drop into the housing provided for this purpose in the carriage 52 since it is already occupied by a set 26 of reaction wells, such that when the arms 54 are released by the wheels 62 they reengage their fingers 58 beneath the rims of the bottom set in the corresponding stack, lifting the stack very slightly.

After the carriage 52 has passed under the last magazine 50, it is brought back towards the front, spreading the arms 54 of each magazine as it goes past, but without capturing any sets 26 of reaction wells, and it returns to its feed position situated in front of the first magazine 50.

The rails 66 supporting the assembly 26 are interrupted immediately before this feed position, such that the set 26 of wells driven by the carriage into this position falls under gravity to a lower level where it escapes from the arms 28 of the carriage, thus allowing the carriage to be reversed to capture a new set 26 of reaction wells.

From the above, it will be understood that the carriage 52 takes the sets 26 of reaction wells located in the first magazine 50 one after another, and then takes them from the second magazine 50 once the first magazine is empty, and then takes them from the third magazine 50 once the first two magazines are empty, it being possible to refill the empty magazines at any moment without there being any need to interrupt the operation of the assay apparatus.

Reference is now made to FIGS. 9 to 11 which are diagrams showing the means for moving the sets of wells transversely at the longitudinal ends of their rectangular paths through the assay apparatus.

At the ends of this path, the rails 38 are extended by bars 72 which define two end positions P1 and P3 where the sets 26 of wells are supported partly by the rails 38 and partly by the bars 72, and an intermediate position P2 which is situated between the end positions P1 and P3 (FIG. 9).

The means for moving the sets 26 of wells in the positions P1, P2, and P3 comprise a transverse vertical plate 74 disposed in the gap between the rails 38 and the bars 72, and guided vertically in a carriage 76 which is itself guided in reciprocating motion on horizontal transverse rods 78 carried by the frame 10, the plate 74 and the carriage 76 being driven by an eccentric motor system.

The system comprises an electric motor 80 having a vertical disk 82 mounted on its outlet shaft, the disk being movable in rotation about its axis 84 and carrying an eccentric wheel 86 which is received in a horizontal slot 88 in the vertical plate 74 and which can move along the edge of a curved slot 90 formed in a vertical wall 92 of the carriage 76.

The curved slot 90 is roughly lemon-shaped, comprising two facing circular arcs 94 which are parallel to the edge of the disk 82 and which correspond to the path of the outer periphery of the wheel 86 as driven by the disk 82, together with two vertical abutments 96 respectively at the top and bottom ends of the circular arcs 94.

These vertical abutments 96 enable the carriage 76 to be moved horizontally from left to right and from right to left in FIG. 9 when the disk 82 is rotated in the direction indicated by the arrow. When the wheel 86 is in the position shown, bearing against the bottom vertical abutment 96, it will move the carriage 76 to the right in FIG. 9 until it bears against the frame 10. During this movement, the vertical plate 74 is moved vertically through a very small distance.

The wheel 86 escapes from the vertical abutment 96 when the carriage 76 is pressed against the frame 10, and it then begins to run along the curved portion 94 of the slot 90, thereby moving the plate 76 vertically upwards without moving the carriage 76. Then, when the wheel 86 comes into abutment against the top vertical abutment 96, it causes the carriage 76 to move to the left in FIG. 9 until it is brought to bear against the frame 10. The wheel 86 then escapes from the top vertical abutment 96 and runs along the curved portion 94 of the slot 90, thereby moving the plate 74 downwards so as to bring it back to the position shown in FIG. 9.

Thus, when the disk 82 and the wheel 86 rotate through 360° about the axis 84, the plate 74 is moved along a path that is substantially rectangular or square, as shown diagrammatically by arrows 98 in FIG. 9.

The top edge 100 of the vertical plate 74 carries three teeth 102 which are spaced apart by a distance equal to the gap between the rails 38 or between the bars 72 and which are designed to engage beneath the side rims 30 of the sets of wells resting on the rails 38 and the bars 72 in order to lift them and disengage them from the rails and bars, while the top edge 100 of the plate 74 engages between the middle two wells 28 in each set 26 (FIG. 10).

When the vertical plate 74 is moved along the path represented by the arrows 98 in FIG. 9, it lifts vertically the top sets 26 of wells located in the positions P3 and P2, it disengages them from the rails and the bars 38 and 72, it brings them into the positions P2 and P1, and then it brings the sets 26 back down vertically and places them on the rails and bars 38 and 72.

The sets 26 of wells carried by the plate 74 are in a position that is relatively stable because their rims 30 are resting on the teeth 102 of the plate and because the top edge 100 of the plate is engaged between the middle two wells 28 in each set 26.

At the longitudinal ends of their rectangular path, the sets 26 are thus moved transversely in pairs through the three positions P3, P2, and P1 by the vertical plate 74 and its drive means, which means are actuated between two advance steps of the sets 26 along the long sides of their rectangular path.

The intermediate position P2 provided adjacent the feed means 24 thus simultaneously constitutes a position for feeding with a new set of wells and a position for ejecting a used set of wells.

As shown diagrammatically in FIG. 12, when a new set 26 of wells is delivered by the carriage 52 into the feed position P2, it simultaneously ejects from this position the set 26 previously occupying it, which set falls into an opening or a hopper slideway (not shown) leading to a box or a dust bin.

When a new set 26 of reaction wells has replaced the used set of wells in position P2, the transverse displacement means provided at this end of the rectangular path move the sets 26 of wells that were in positions P2 and P3 into positions P1 and P2, respectively, while at the other end of the apparatus, the corresponding means for transverse displacement move the sets of reaction wells from positions P2 and P3 into positions P1 and P2, respectively.

The sets 26 are moved stepwise along the long sides of the rectangular path, as shown in FIG. 14 until sets 26 of reaction wells again occupy the positions P3 as shown in FIG. 15. The means for moving these sets transversely are then actuated to transfer the sets of reaction wells that are to be found in positions P2 and P3 into positions P1 and P2 respectively.

In this apparatus, a set 26 of reaction wells delivered to the feed position P2 must make two complete trips round the entire rectangular path for a single-reagent assay, and three trips for a two-reagent assay, prior to being ejected as shown in FIG. 12.

Under the same conditions as those described in international application WO 96/14582, the apparatus of the invention can operate at a rate of 120 assays per hour, and it can do so entirely automatically.

We claim:

1. Automatic apparatus for immunological assay comprising means for supporting, guiding, and displacing sets of reaction wells stepwise along a path comprising a predetermined number of positions, means for supporting samples to be analyzed, means for supporting reagents, means for taking determined quantities of samples and of reagents and for injecting these quantities into the reaction wells, and means for washing the wells, means for reading results of the assay, and means for feeding sets of reaction wells and for rejecting used sets of wells, wherein the path for the sets of reaction wells is rectangular in shape comprising two long sides defined by parallel rectilinear rails for supporting and guiding sets of wells, and two short sides defined by means for displacing sets of wells transversely through three positions comprising two end positions on the long sides of the above-mentioned path and one intermediate position which constitutes an ejection position for a used set of wells and a feed position for a new set of wells.

2. Apparatus according to claim 1, wherein the means for displacing sets of wells transversely displace the sets of wells in pairs through the three above-mentioned positions, one set of wells being displaced from an end position to the intermediate position and the other set of wells being displaced from the intermediate position to the other end position.

3. Apparatus according to claim 1, wherein the means for displacing the sets of wells transversely are actuated during intervals between two displacement steps of the sets of wells along the long sides of the above-mentioned path.

4. Apparatus according to claim 2, wherein the transverse displacement means comprise grasping means for taking two sets of wells and means for lifting, transversely displacing, and lowering the grasping means.

5. Apparatus according to claim 4, wherein the grasping means comprise a vertical transverse plate displaceable beneath the sets of reaction wells, to lift them by engaging between two wells in each set.

6. Apparatus according to claim 5, wherein the transverse plate is guided in vertical translation in a carriage which is displaceable along a short side of the rectangular path for the sets of wells by drive means comprising a rotary disk having an eccentric wheel guided in a horizontal slot of the vertical plate and in a curved slot in a wall of the carriage.

7. Apparatus according to claim 1, wherein the means for feeding new sets of wells comprise magazines for storing stacks of sets of wells interfitting in one another, a carriage for capturing and horizontally displacing a set of wells, guided beneath the open bottom ends of the magazines and displaceable to the above-mentioned intermediate position forming the feed and ejection position, the magazines being fitted with pivoting arms which hold the bottom set of wells in each stored stack and which are spread apart by the carriage as it passes beneath the stack in order to release the bottom set of wells from the stack and allow it to fall under gravity into a housing formed in the carriage, providing the housing is not already occupied by another set of reaction wells.

8. Apparatus according to claim 7, wherein the storage magazines are in alignment with said feed and ejection intermediate position.

9. Apparatus according to claim 1, wherein the means for ejecting used sets of wells comprise a slideway or a chute opening formed in alignment with the above-mentioned intermediate position, such that the feed means delivering a new set of wells into said intermediate position causes the used set of wells occupying said intermediate position to be pushed to the slideway or chute opening.

10. Apparatus according to claim 1, wherein the means for displacing the sets of wells along the long sides of the above-mentioned path comprise a cog belt engaging ribs of longitudinal rims on the sets of wells, said belt being guided along the outer rail of each long side of the above-mentioned path.

11. Apparatus according to claim 1, wherein the sets of wells include longitudinal rims whereby they rest on the rails defining the long sides of the above-mentioned path, said rims including, on either side of the wells, orifices for receiving moving positioning fingers disposed in association with the above-mentioned washing means.

* * * * *